US00PP25344P3

(12) United States Plant Patent
Egger

(10) Patent No.: US PP25,344 P3
(45) Date of Patent: Mar. 10, 2015

(54) *AGASTACHE* PLANT NAMED 'KUDOS SILVER BLUE'

(50) Latin Name: ***Agastache* hybrid**
Varietal Denomination: Kudos Silver Blue

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 120 days.

(21) Appl. No.: 13/986,503

(22) Filed: May 9, 2013

(65) Prior Publication Data

US 2014/0338087 P1 Nov. 13, 2014

(51) Int. Cl.
*A01H 5/00* (2006.01)

(52) U.S. Cl.
USPC ..... Plt./399

(58) Field of Classification Search
CPC ..... A01H 5/02
USPC ..... Plt./399
See application file for complete search history.

(56) References Cited

PUBLICATIONS

Greenhouse Growers. Terra Nova Nurseries Introduces *Agastache* Kudos Series, (Nov. 21, 2012) retrieved on Oct. 28, 2014, retrieved from the Internet at <www.greenhousegrower.com/varieties/terra-nova-nurseries-introduces-agastache-kudos-series/> 2 pp.*

* cited by examiner

*Primary Examiner* — June Hwu
(74) *Attorney, Agent, or Firm* — Klarquist Sparkman, LLP

(57) ABSTRACT

A new and distinct form of *Agastache* plant characterized by light purple flowers in large inflorescences, a long bloom time, a very short, compact habit, good winter hardiness, and excellent vigor.

1 Drawing Sheet

Botanical denomination: *Agastache* hybrid.
Variety designation: 'Kudos Silver Blue'.

BACKGROUND OF THE INVENTION

The present invention relates to a new and distinct cultivar of *Agastache*, given the name, 'Kudos Silver Blue'. *Agastache* is in the family Lamiaceae. This new cultivar is one of several selections of new *Agastache* using hardy and dwarf *Agastache* species in the breeding lines to provide hardiness and compactness. The new cultivar is a selection from the cross between the proprietary seedlings 55-2 (unpatented), as the seed parent, and 54-1 (unpatented), as the pollen parent. The new cultivar was selected for its compact habit, hardiness, and light purple flowers.

Compared to the seed parent, *Agastache* 55-2 (unpatented) the new cultivar is shorter and has light purple rather than dark purple pink flowers.

Compared to the pollen parent, *Agastache* 54-1 (unpatented), the new cultivar has light purple rather than orange pink flowers.

Compared to *Agastache* 'Violet Vision', U.S. patent application Ser. No. 13/986,386, the new cultivar has lighter flower color and a shorter and more spreading habit.

This plant exhibits the following characteristics that make it unique:

1. light purple flowers in large inflorescences,
2. a long bloom time,
3. a very short, compact habit,
4. good winter hardiness, and
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar grown in a one gallon container in full sun in Canby, Oreg.

FIG. 2 shows a bed of nine-month-old *Agastache* 'Kudos Silver Blue' growing in the field in mid-summer in Canby, Oreg.

DETAILED PLANT DESCRIPTION

The following is a detailed description of the new *Agastache* cultivar based on observations of 9-month-old specimens in early September growing in full sun in the trial field. in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form*.—Upright.

*Type*.—Herbaceous perennial.

*Cold hardiness*.—USDA Zone 6-10.

*Size*.—Grows to 68 cm wide and 50 cm tall to the top of the flowers.

*Vigor*.—Excellent.

*Branching*.—About 20 main stems from the base, these branch at every node.

*Stem*.—Square in cross section, grows to 5 mm wide and 23 cm tall to the first flower, pubescent, internodes range from 1 to 2 cm long, Yellow Green 146B.

*Roots*.—White 155B, fibrous, plants root easily from stem tip cuttings.

Leaf:

*Type*.—Simple.

*Arrangement*.—Opposite.

*Shape*.—Ovate.

*Venation*.—Pinnate.

*Margins*.—Coarsely serrate.

*Apex*.—Acute.

*Base*.—Cuneate.

*Blade size*.—Grows to 50 mm long and 38 mm wide.

*Surface texture*.—Pubescent on both sides.

*Petiole description*.—10 mm long and 2 mm wide, pubescent, Yellow Green 147B.

*Leaf color*.—Top side Green 137A with vein Green 137C, bottom side closest to Yellow Green 147B with vein 147C.

*Fragrance*.—Aromatic.

Inflorescence:

*Type*.—Terminal spike with up to 12 whorls.

*Number of flowers*.—Up to 600 per spike.

*Size of inflorescence*.—Grows to 14 cm tall and 4.5 cm wide.

*Peduncle*.—Grows to 16 cm tall and 3 mm wide, pubescent, Yellow Green 146A.

*Pedicel*.—Grows to 1 mm long, pubescent, Yellow Green 146B.

*Bloom period*.—June through frost in Canby, Oreg.

Flower bud:

*Size*.—15 mm long and 3 mm wide at the widest point prior to opening.

*Description*.—Tubular.

*Surface texture*.—Pubescent.

*Color*.—Closest to Violet 84A.

Flower:

*Type*.—Zygomorphic.

*Shape*.—Bilabiate, tubular.

*Size*.—20 mm long and 7 mm wide.

*Corolla description*.—16 mm long and spreads to 7 mm wide; color both sides Violet 85A; pubescent inside and outside, tube 11 mm long and 1 mm to 4 mm wide; 2 upper lobes joined 3 mm long and 3 mm wide, each ovate, tips obtuse, margin entire; three lower lobes, two spreading sideways and curve out slightly, each 1.5 mm long and 3 mm wide, tip obtuse, margin entire; bottom lobe, reflexed, broadly obovate, notched at the tip, margin undulate, 5 mm wide and 2.5 mm deep.

*Calyx description*.—Campanulate, 6.5 mm long and 3.5 mm wide, pubescent outside and glabrous inside, 5 lobed, lobes ovate, 2 mm long, entire, acuminate, colored when young Greyed Orange 177A at tip blending to Yellow Green 147C becoming Yellow Green 147C all over with age.

*Pistil description*.—20 mm long, ovary 1 mm long, Yellow Green 145D, style 19 mm long, White NN155B except top 4 mm where Violet 86B, stigma two-parted, 1 mm deep, Violet 86B.

*Stamen description*.—4 in number, paired and exerted, top two 7 mm long and bottom two 5 mm long, filaments Violet 85B, anthers 0.3 mm long, Violet Blue 86A, pollen White N155A.

*Fragrance*.—Aromatic.

*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

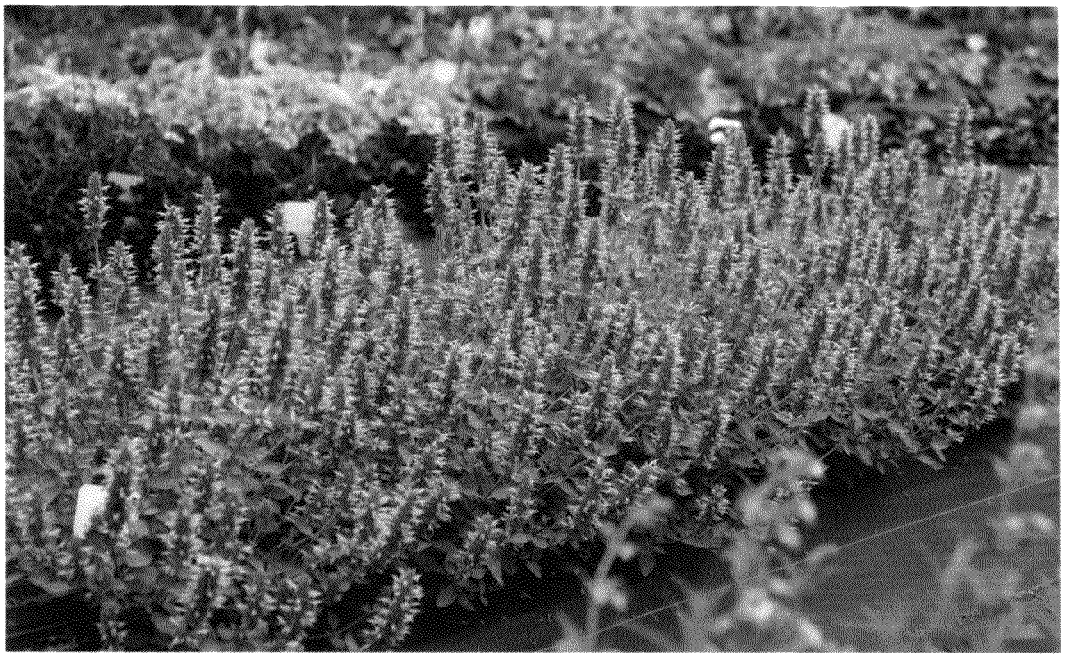

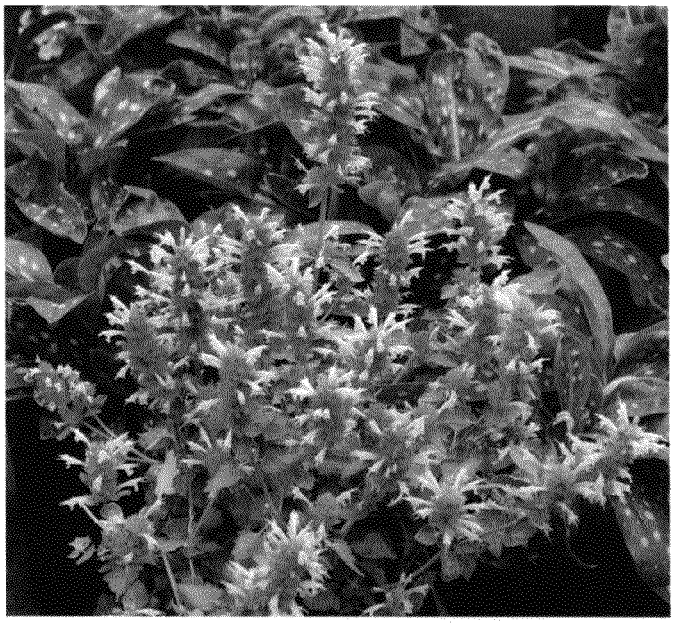
FIG.1 above, FIG. 2 below